United States Patent [19]
Witzel et al.

[11] 4,380,645
[45] Apr. 19, 1983

[54] PROCESS FOR PREPARING BENZOXEPINO- OR BENZTHIAPINO[4,3-B]PYRROLE-2-ACETIC ACIDS

[75] Inventors: Bruce E. Witzel, Rahway; Paul E. Finke, Metuchen; Debra L. Allison, Scotch Plains, all of N.J.

[73] Assignee: Merck & Co., Inc., Rahway, N.J.

[21] Appl. No.: 329,842

[22] Filed: Dec. 11, 1981

[51] Int. Cl.$^3$ ................ C07D 491/044; C07D 495/04
[52] U.S. Cl. ..................................... 548/430; 548/533
[58] Field of Search ...................... 260/326.47, 326.46, 260/326.28, 326.29; 548/430, 533

[56] References Cited
U.S. PATENT DOCUMENTS
3,752,826  8/1973  Carson .............................. 260/326.3

OTHER PUBLICATIONS

Carson et al., *J. Med. Chem.*, 16, No. 2, 173 (1973).
H. Kondo et al., *J. Pharm. Soc. Japan*, 57, 1 at p. 3 (1937).
R. Chong et al., *Aust. J. Chem.*, 20, 935–950 at 946 (1967).
Ackrell et al., J. Heterocyclic Chem., 17, 1081 (1980).

*Primary Examiner*—Richard Raymond
*Attorney, Agent, or Firm*—Theresa Y. Cheng; Mario A. Monaco

[57] ABSTRACT

Improved yields of Benzoxepino- or Benzthiapino[4,3-b]pyrrole-2-acetic acids have been achieved from processes based on modifications performed on a pyrrole carboxylic ester rather than on a pyrrole-α-oxoacetate.

10 Claims, No Drawings

PROCESS FOR PREPARING BENZOXEPINO- OR BENZTHIAPINO[4,3-B]PYRROLE-2-ACETIC ACIDS

BACKGROUND OF THE INVENTION

Benzoxepino or benzthiapino[4,3-b]-pyrrole-2-acetic acids, for example, 1,7-dimethyl-4,10-dihydro-10-oxo-1H-[1]-benzoxepino[4,3-b]pyrrole-2-acetic acid

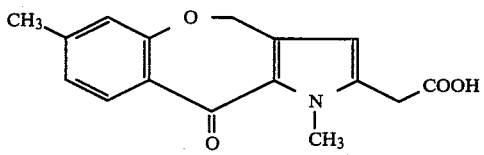

are found to be potent analgesic and anti-inflammatory agents with very low ulcerogenic side effect. These compounds and the composition, method of use and process for preparation thereof have been the subject matter of a pending application U.S. Ser. No. 279,140 filed June 30, 1981. Although the compounds have been prepared by a satisfactory method as disclosed in U.S. Ser. No. 279,140, involving the intermediate pyrrole α-oxoacetate (I),

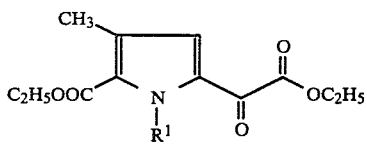

the overall yields have been unsatisfactory and therefore economically unviable. Accordingly, it is the object of this invention to provide new and improved processes for making the active compounds.

DETAILED DESCRIPTION OF THE INVENTION

The present invention relates to novel processes for the preparation of benzoxepino or benzthiapino[4,3-b]pyrrole-2-acetic acids of the structural formula (II)

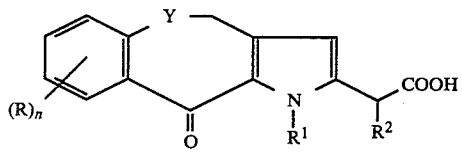

wherein
Y is O or S;
n is an integer from 1 to 4;
R is
 (a) hydrogen;
 (b) lower alkyl especially $C_{1-6}$alkyl, e.g., methyl, ethyl, isopropyl, t-butyl, pentyl and cyclohexyl;
 (c) halo-loweralkyl wherein halo is fluoro, and loweralkyl as defined in (b);
 (d) hydroxy or loweralkoxy especially $C_{1-6}$alkoxy such as methoxy, ethoxy, allyloxy, t-butoxy, cyclopentyloxy or hexyloxy;
 (e) —OCH$_2$O— when there are two Rs and they join together to form the methylene dioxy group;
 (f) halo such as fluoro, chloro, bromo or iodo;
 (g) lower alkylthio especially $C_{1-6}$alkylthio, e.g., methylthio, ethylthio, and isopropylthio;
 (h) lower alkylsulfinyl especially $C_{1-3}$alkylsulfinyl, e.g., methylsulfinyl, ethylsulfinyl, and propylsulfinyl;
 (i) lower alkylsulfonyl, e.g., methylsulfonyl, ethylsulfonyl, and propylsulfonyl; or
 (j) lower alkenyl especially $C_{2-6}$alkenyl such as ethenyl, propenyl, 2-butenyl, pentenyl, allyl and hexenyl;
$R^1$ is
 (a) hydrogen;
 (b) lower alkyl as previously defined;
 (c) lower alkenyl as previously defined; or
 (d) aralkyl such as benzyl, phenethyl; and
$R^2$ is
 (a) hydrogen;
 (b) lower alkyl as previously defined;
 (c) halo especially fluoro or chloro;
 (d) lower alkoxy as previously defined.

More particularly the present process is for preparing a compound of formula (II) wherein:
Y is O;
R is
 (a) hydrogen;
 (b) $C_{1-4}$alkyl such as methyl, ethyl, isopropyl or t-butyl;
 (c) halo-$C_{1-3}$alkyl such as trifluoromethyl;
 (d) $C_{1-3}$alkoxy such as methoxy, ethoxy, propoxy, and methylene dioxy;
 (e) chloro or fluoro;
 (f) $C_{1-3}$alkylthio such as methylthio, ethylthio;
$R^1$ is hydrogen, $C_{1-3}$alkyl such as methyl, ethyl or propyl; and
$R^2$ is
 (a) hydrogen;
 (b) $C_{1-3}$alkyl as previously defined;
 (c) fluoro; or
 (d) $C_{1-3}$alkoxy as previously defined.

Even more particularly the present process is for preparing a compound of formula (II) wherein
Y is O;
$R_1$ is $C_{1-4}$alkyl or $C_{1-4}$alkoxy;
$R^1$ is $C_{1-3}$alkyl; and
$R^2$ is hydrogen or methyl.

According to the new process, the compounds of formula (II) are prepared in four steps as summarized below in Scheme I:

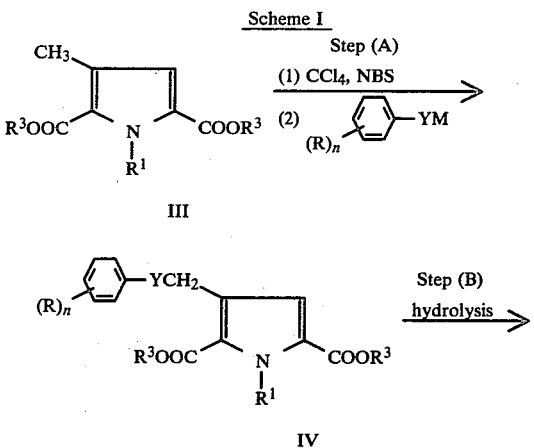

-continued
Scheme I

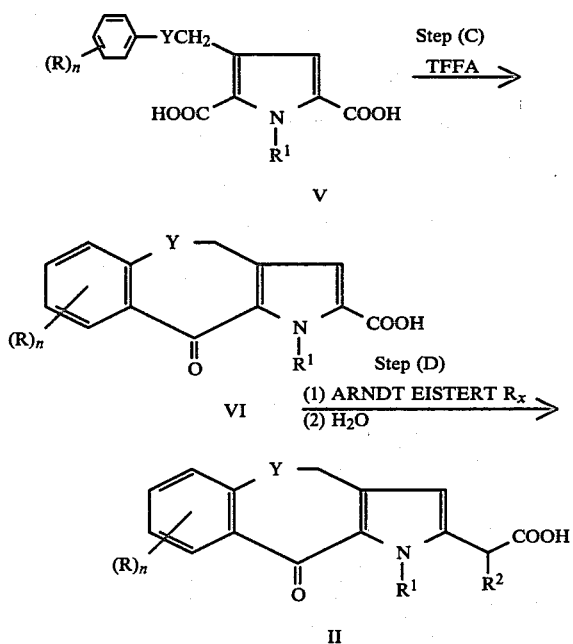

(a) 4-methyl-1,5-dialkoxycarbonyl pyrrole of the formula (III) wherein $R^3$ is loweralkyl as previously defined or other protecting groups for carboxylic acids is halogenated with N-bromosuccinimide or other suitable halogenating agents in an inert solvent which may be selected from chlorinated hydrocarbons such as carbon tetrachloride, methylene chloride, chloroform, or hydrocarbons such as benzene or cyclohexane. The halogenation may be carried out at a temperature from about 0° C. to about 100° C., preferably at 20° to 80° C. or the boiling point of the solvent and may be catalyzed by light or a standard free radical catalyst, such as dibenzoyl peroxide. The time of reaction is not critical and the reaction is usually carried out until it is substantially complete. The 4-halomethyl intermediate is subsequently isolated and treated with a phenoxide or thiaphenolate of formula

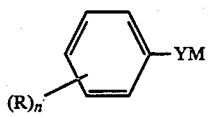

wherein R, n and Y are as previously defined and M is an alkali metal cation, for example Na+, K+ or Li+.

(b) The resulting 4-$(R)_n$—$C_6H_{5-n}$—Y—$CH_2$— derivative, (IV), is converted to the diacid (V) via conventional procedures, for example hydrolysis in the presence of a base such as sodium hydroxide.

(c) The resultant diacid (V) is treated with a condensing agent, for example, trifluoroacetic anhydride (TFAA), with or without trifluoroacetic acid (TFA) or suitable Lewis acid (aluminum chloride, stannic chloride, etc.) to give the ring-closed product, i.e., tricyclic benzoxepino or benzthiazino [4,3-b]pyrrolecarboxylic acid (VI). The reaction may be carried out with or without a solvent such as methylene chloride, 1,2-dichloroethane, excess TFA, etc. Alternately, standard Friedel-Crafts conditions may be used to effect the closure, such as a suitable Lewis acid on the corresponding acid chloride, or the closure may be carried out using a polyphosphoric acid or equivalent type system. In general, the use of TFAA with TFA or aluminum chloride is preferred, the reaction conducted under mild conditions at temperatures as low as −20° C. to 70° C., preferably at about 0° C. to 35° C.

(d) The resultant tricyclic compound (VI) is converted by Arndt-Eistert reaction (See Org. Reactions, I, Chap. 2, p. 53) or other known, classical, sequences for chain extension of carboxylic acids, generally through condensation or substitution reactions of the corresponding acid chlorides, aldehydes or alcohols or derivatives thereof to compounds of formula (II). According to the Arndt Eistert procedure, the tricyclic carboxylic acid (VI) is converted by way of its chloride into diazoketones which in turn rearrange to the homologous carboxylic acid (II). The reagent used for diazoketone formation is usually a diazoalkane, e.g., diazomethane (freshly generated from N-methyl-N-nitrosourea, etc.), or diazoethane. After the diazoketone of (VI) is formed, it is decomposed, in the presence of a finely divided salt of silver, copper, or platinum, in water or in an alcohol such as methanol or ethanol. When the above decomposition is conducted in water, it leads to a homologous acid. However, when an alcohol is used instead of water, an ester of the homologous acid is formed first which is then hydrolyzed to the acid of formula (II). Sometimes, it may be desirable to decompose the diazoalkane in ammonia or an amine to prepare first the amide of the homologous acid and then hydrolyze this product to the acid.

Alternatively, the decomposition may be carried out in a high boiling alcohol such as benzyl alcohol in the presence of collidine or other strong organic bases.

The preferred embodiment of this step is to treat compound (VI) with thionyl chloride, oxalyl chloride or the like to form the corresponding acid chloride. The chlorination is usually carried out in an anhydrous inert solvent, e.g., methylene chloride (sometimes containing a trace of N,N-dimethylformamide) at about 10° C. to about 75° C., preferably at ambient temperatures until the reaction is substantially complete. The crude acid chloride is then treated with freshly prepared diazomethane or diazoethane at low temperatures, preferably at about −5° C. to about 25° C. until most starting material has been converted to diazoketone. The resultant diazo compound is subsequently treated with an excess of anhydrous methanol or ethanol containing silver oxide and/or silver nitrate. Generally, the rearrangement requires mild heating, i.e., heating at from about 35° C. to about 100° C., preferably at reflux of the reaction mixture. Under optimum conditions, the above chlorination-diazoketone formation-rearrangement sequence may be completed in about 5 to about 72 hours.

The overall yield of the new process is estimated to be about 40-fold of the pyrrole-α-oxoacetate process as described in the copending application U.S. Ser. No. 279,140.

Alternatively, the novel compounds of formula (II) may also be prepared by the synthetic scheme as shown below

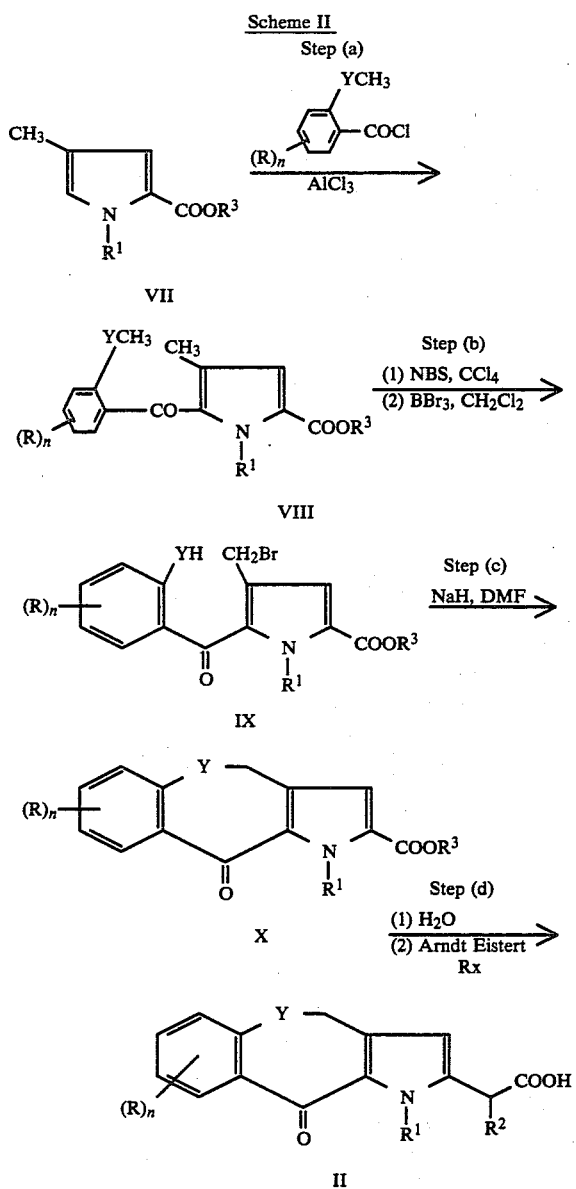

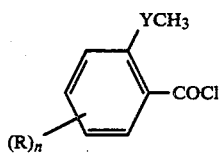

hours. Under optimum conditions it may only require about 1–10 hours.

(b) The resultant 5-benzoyl derivative (VIII) from step (a) is halogenated as described previously followed by cleavage of the —YCH₃ group to afford compound (IX). The cleavage may be carried out by first treating the methoxy compound (VIII) with a strong Lewis acid, e.g., boron tribromide, followed by treatment with water.

(c) The resultant —YH derivative (IX) from Step (b) is treated with a strong base, for example, sodium hydride in DMF or other commonly used inert aprotic solvent, to form the nucleophilic phenolate anion which in turn displaces the bromo group of the 4-bromomethyl function attached to the pyrrole ring. This intramolecular cyclization is usually carried out under low temperatures from about −50° C. to about 50° C., preferably from about −20° C. to about 20° C. The reaction time is not critical as the reaction is usually monitored by analytical methods such as thin-layer chromatography until it is substantially complete.

(d) The tricyclic compound (X) resulting from Step (c) is hydrolyzed and then converted to the desired compounds of formula (II) via the Arndt Eistert or alternative reactions as described previously.

The starting materials of the new processes, (III) and (VII), are readily obtained from commercially available materials, e.g., 1-methyl-pyrrole 2-carboxylic acid, glycine ethyl ester hydrochloride, acetone, and diethyl oxalate, as shown below in schemes III and IV:

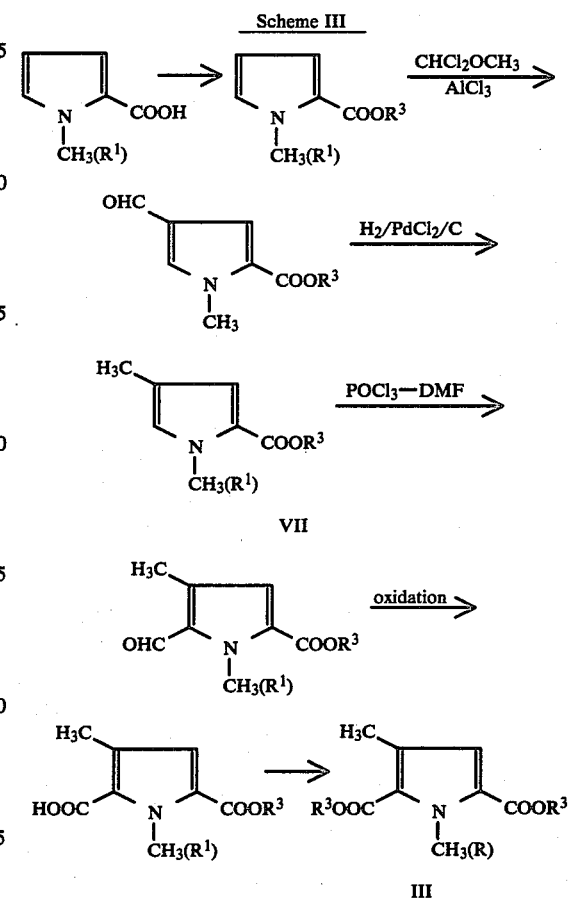

The alternative process comprises four steps:
(a) a 4-methylpyrrole-2-carboxylic acid ester (VII) is treated with a 2—YCH₃— benzoyl chloride of formula under Friedel-Craft reaction conditions well-known in the art. For example, mixing the substrates and a catalyst such as AlCl₃, CF₃SO₃H, or other commonly used Lewis acid in an inert solvent such as dichloroethane and nitromethane or a mixture thereof at about −30° C. or at ambient temperatures, preferably at about −10° C. to about 15° C. until the acylation is substantially complete. The reaction usually takes about 1 to about 48

Scheme IV

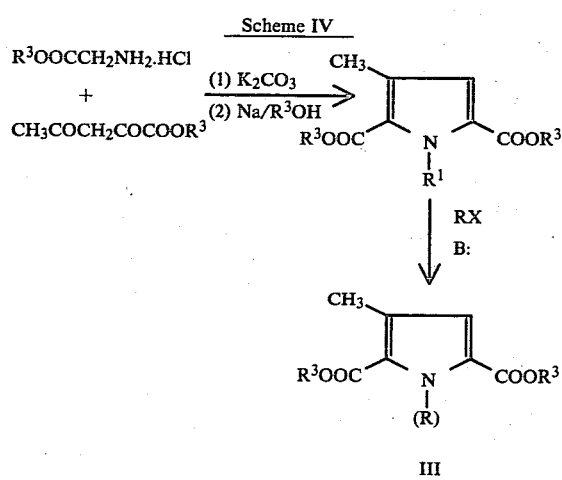

III

The reaction sequence represented in Scheme III is self-explanatory and is especially usefull for intermediate VII. The preferred reaction sequence described in Scheme IV is a much shorter and efficient method for preparing the starting material III. The condensation of α-amino-ketones and β-diketones in aqueous sodium hydroxide for 5 days to give 3-methyl-5-carbethoxypyrrole-2-carboxylic acid has been reported by H. Kondo et al., in J. Pharm. Soc. Japan, 57, 1–5 (1937); C. A. 31, 103$^b$ and 7055 (1937). However, when the same procedure was applied to α-aminoester of Scheme IV, only a trace amount of diethyl 3-methyl-pyrrole-2,5-dicarboxylate was obtained. By the modified procedure of this invention, the condensation is carried out in two stages; (1) with a weak base suspended in a refluxing, inert aprotic solvent, e.g., benzene, toluene and xylene, the weak base may be sodium carbonate, potassium carbonate, sodium bicarbonate, potassium bicarbonate or the like; and (2) with an alkali metal such as sodium or lithium in a loweralkanol especially $C_{1-6}$ alkanol, for example, methanol, ethanol, isopropyl alcohol and t-butyl alcohol. The two-stage condensation is usually performed in one-pot without isolation of intermediates. The yield of this improved procedure ranges from about 50–55% on molar basis.

The following examples serve to illustrate but not limit the present invention.

EXAMPLE 1

Methyl 1,4-dimethylpyrrole-2-carboxylate

Step A: Preparation of Methyl 4-formyl-1-methylpyrrole-2-carboxylate

To a mixture of methyl 1-methylpyrrole-2-carboxylate (5.0 g, 0.036 m) and 11.4 g anhydrous aluminum chloride in 150 ml of 1:1 1,2-dichloroethane and nitromethane at −20° C. was added over two minutes a solution of dichloromethyl methylether (3.9 ml, 0.043 m) in 1,2-dichloroethane (20 ml). The resultant mixture was stirred at −10° to −30° C. for 3 hours, quenched with excess ice-water, the resultant mixture extracted well with ether, and the combined ether extracts washed two times with water, passed through a small layer of sodium sulfate-silica gel, and concentrated in vacuo to 5.4 g (90%) of methyl 4-formyl-1-methylpyrrole-2-carboxylate, m.p. 95°–97° C.

Step B: Preparation of Methyl 1,4-dimethylpyrrole-2-carboxylate

A mixture of 3.0 g (0.018 m) methyl 4-formyl-1-methylpyrrole-2-carboxylate, 0.75 g 10% palladium chloride on carbon, and ethanol (100 ml) was reduced under a 40 p.s.i. hydrogen atmosphere at room temperature until theoretical hydrogen uptake was reached. The mixture was filtered and concentrated to yield 2.5 g of methyl 1,4-dimethyllpyrrole-2-carboxylate as a yellow oil.

Following substantially the same procedure as described above in Steps A and B but substituting for the methyl 1-methylpyrrole-2-carboxylate used therein, other 1-alkyl substituted pyrrole-2-carboxylates as shown below in Table I, there are prepared corresponding 1,4-disubstituted pyrrole-2-carboxylates (1) to (5) also shown in Table I.

TABLE I

| Starting Material Compound No. | $R^1$ | Product $R^3$ |
|---|---|---|
| (1) | $CH_3$ | $C_2H_5$ |
| (2) | $C_2H_5$ | $n\text{-}C_3H_7$ |
| (3) | $CH_3$— | $n\text{-}C_4H_9$ |
| (4) | $n\text{-}C_3H_7$ | $CH_3$ |
| (5) | $n\text{-}C_4H_9$ | $i\text{-}C_3H_7$ |

EXAMPLE 2

Dimethyl 1,3-dimethylpyrrole-2,5-dicarboxylate

Step A: Preparation of Methyl 1,4-dimethyl-5-formylpyrrole-2-carboxylate

A solution of methyl 1,4-dimethylpyrrole-2-carboxylate (2.5 g, 0.016 m) in 20 ml of dried 1,2-dichloroethane was added over two minutes to a stirred mixture of phosphorous oxychloride (2.3 ml) and dried, N,N-dimethylformamide (1.94 ml) in 50 ml of dichloroethane, and the resultant mixture heated at 90° C. (bath temperature) for 45 minutes. The cooled reaction mixture was treated with excess ice-water and ether, 10% aqueous sodium carbonate (50 ml) added, the ether layer removed and the aqueous phase re-extracted two times with fresh ether, and the combined ether layers washed well with water and dried over anhydrous sodium sulfate. Concentration of the ether solution yielded 2.48 g (84%) of methyl 1,4-dimethyl-5-formylpyrrole-2-carboxylate as a yellow solid.

Step B: Preparation of Dimethyl 1,3-dimethylpyrrole-2,5-dicarboxylate

To a solution of methyl 1,4-dimethyl-5-formylpyrrole-2-carboxylate (0.3 g, 0.0016 m) in acetone (10 ml) at room temperature was added over 15 minutes a solution of potassium permanganate (0.52 g, 0.0033 m) in 1:1 water-acetone (10 ml), and the resulting mixture allowed to stir for 1.5 hours. The reaction mixture was then diluted with water (100 ml), treated with enough sodium sulfite to reduce the excess permanganate, filtered, and the filtrate acidified with dilute hydrochloric acid. The resulting precipitate was filtered, washed well with water and dried to give 0.20 g (64%) of methyl 5-carboxy-1,4-dimethylpyrrole-2-carboxylate.

Treatment of this acid in the standard fashion with diazomethane yielded dimethyl 1,3-dimethylpyrrole-2,5-dicarboxylate, m.p. 86.5°–87° C.

Following substantially the same procedure as described above in steps A and B but substituting for the starting material, methyl 1,4-dimethylpyrrole-2-carboxylate, the various 1,4-disubstituted pyrrole-2-carboxylates (1) to (5) of Table I, there are prepared the following diesters of 1-substituted-3-methylpyrrole-2,5-dicarboxylates.

TABLE II $$CH_3OOC-\underset{\underset{R^1}{|}}{N}-COOR^3 \text{ (with CH}_3\text{ on ring)}$$

| R$^1$ | R$^3$ |
|---|---|
| CH$_3$ | CH$_3$ |
| C$_2$H$_5$ | n-C$_3$H$_7$ |
| CH$_3$ | n-C$_4$H$_9$ |
| n-CH$_3$H$_7$ | CH$_3$ |
| n-C$_4$H$_9$ | i-C$_3$H$_7$ |

EXAMPLE 3

Diethyl 1,3-dimethylpyrrole-2,5-dicarboxylate

Step A: Preparation of Diethyl 3-methylpyrrole-2,5-dicarboxylate

To a stirred, refluxing mixture of ethyl glycinate hydrochloride (100 g, 0.71 m), ethyl oxalacetone (112.8 g, 0.71 m) and benzene (650 ml) under a nitrogen atmosphere was added finely powdered anhydrous potassium carbonate (50 g, 0.36 m) in five portions over ca. one hour, the eliminated water being collected in a Dean-Stark trap. When the theoretical amount of water had been collected, the mixture was cooled to less than 5° C., 750 ml of dried ethanol dried, the solution recooled to 5° C., and sodium metal (16.5 g, 0.71 m) added in small pieces as rapidly as possible while maintaining the temperature at less than 40° C. with external cooling. After stirring in an ice-bath for an additional 0.5 hour, the reaction mixture was poured into a 5 liter separatory funnel containing ether (1 liter) and water (2 liters), the layers separated, the aqueous layer reextracted well with ether and the combined ether layers washed with water and saturated sodium chloride solution. Concentration of the dried ether layer yielded 73 g of diethyl 3-methylpyrrole-2,5-dicarboxylate as a tan to brown solid.

Step B: Preparation of Diethyl 1,3-dimethylpyrrole-2,5-dicarboxylate

The diethyl 3-methylpyrrole-2,5-dicarboxylate obtained in Step A was taken up in dried N,N-dimethylformamide (100 ml) and added dropwise over 10 minutes, under nitrogen to an ice-cooled suspension of washed (hexane) sodium hydride (from 16.2 g, 0.41 m of 60% sodium hydride in mineral oil dispersion) in dried N,N-dimethylformamide (400 ml). The resulting mixture was then stirred without cooling for 1 hour, recooled in an ice-bath and treated dropwise over ca. 15 minutes with methyl iodide (30.3 ml, 0.49 m). After stirring for an additional 30 minutes, the mixture was slowly poured into a separatory funnel containing ether (0.5 liter) and water (1 liter). The separated ether layer was washed with water and saturated sodium chloride solution, dried, and concentrated to a tan solid. Purification via chromatography (silica gel/hexane-EtOAc) yielded diethyl 1,3-dimethylpyrrole-2,5-dicarboxylate (75 g) as a white solid, m.p. 48°–48.5° C.

Following substantially the same procedures as described above but substituting the methyl iodide used therein with the alkyl halides listed below in Table III, there are obtained the corresponding diethyl 1-substituted 3-methylpyrrole-2,5-dicarboxylates also shown in Table IV.

TABLE III $$H_5C_2OOC-\underset{\underset{R^1}{|}}{N}-COOC_2H_5 \text{ (with CH}_3\text{ on ring)}$$

| R$^1$X | R$^1$ |
|---|---|
| ethyl iodide | C$_2$H$_5$— |
| allyl bromide | CH$_2$=CH—CH$_2$— |
| benzyl bromide | C$_6$H$_5$CH$_2$— |

EXAMPLE 4

4,10-Dihydro-1,7-dimethyl-10-oxo-1H[1]benzoxepino[4,3-b]pyrrole-2-acetic Acid

Step A: Preparation of Dimethyl 1-methyl-3-[(m-methylphenoxy)methyl]pyrrole-2,5-dicarboxylate To a solution of dimethyl 1,3-dimethylpyrrole-2,5-dicarboxylate (0.7 g, 0.0033 m) in carbon tetrachloride (15 ml) at room temperature was added N-bromosuccinimide (0.71 g) and a few tiny crystals of dibenzoylperoxide. The stirred mixture was set in an oil-bath at 95° C., and a few crystals of dibenzoylperoxide added every twenty minutes until all the N-bromosuccinimide was consumed. The cooled reaction mixture was then filtered and the solvent removed in vacuo to yield 1.0 g of a pale yellow solid, which was taken up in 8 ml of dry, degassed N,N-dimethylformamide and added dropwise over 10 minutes to a stirred, ice-cooled solution of sodium m-cresolate (prepared from 0.43 g m-cresol and 0.18 g 57% sodium hydride dispersion in 12 ml dimethylformamide) under a nitrogen atmosphere. After 2.5 hours, dried ether (50 ml) was added, the mixture added to ice-water (ca. 300 ml), let stir ca. 10 minutes, the layers separated, and the ether layer washed three times with fresh water. Concentration of the ether layer followed by trituration of the residue with methanol yielded dimethyl 1-methyl-3-[(m-methoxyphenoxy)methyl]-pyrrole-2,5-dicarboxylate in 50–70% yield.

Following substantially the same procedure but substituting for the dimethyl 1,3-dimethylpyrrole-2,5-dicarboxylate used therein the corresponding diethyl carboxylate, there is obtained diethyl 1-methyl-3-[(m-methylphenoxy)methyl]pyrrole-2,5-dicarboxylate.

Step B: Preparation of 1-Methyl-3-[(m-methylphenoxy)methyl]pyrrole-2,5-dicarboxylic acid.

To a stirred suspension of dimethyl 1-methyl-3-[(m-methylphenoxy)methyl]pyrrole-2,5-dicarboxylate (0.32 g, 0.001 m) in a mixture of methanol (10 ml) and water (6 ml), ice cooling, was added under a nitrogen atmosphere 2.5 N sodium hydroxide solution (1.2 ml). The mixture was allowed to come to room temperature, and then set in an oil-bath at 50° C., the temperature of the bath raised to 75° C., and kept at this temperature for ca. one hour. After stirring overnight at ambient temperature, water (55 ml) was added over 5 minutes, the mixture filtered, the volume of the filtrate adjusted to 100 ml with water, and the stirred filtrate acidified dropwise with 2 ml of 2 N hydrochloride acid. After aging for 20 minutes, the mixture was filtered, the precipitate washed with water and dried to give 0.27 g (90%) of 1-methyl-3-[(m-methylphenoxy)methyl]-pyrrole-2,5-dicarboxylic acid.

Step C: Preparation of 4,10-Dihydro-1,7-dimethyl-10-oxo-1H[1]-benzoxepino[4,3-b]pyrrole-2-carboxylic acid.

To a stirred ice-bath cooled portion of trifluoroacetic anhydride (30 ml) was added 1-methyl-3-[(m-methylphenoxy)methyl]pyrrole-2,5-dicarboxylic acid (1.0 g) all at once, the mixture stirred 0.5 hour, the ice-bath removed, and the reaction mixture stirred at room temperature. After ca. 3 hours, trifluoroacetic acid (35 ml) was added, and the mixture allowed to stir at ambient temperature. After three hours the reaction mixture was added to excess stirred ice-water, the aged mixture filtered, washed well with water and dried to give crude 4,10-dihydro-1,7-dimethyl-10-oxo-1H[1]-benzoxepino[4,3-b]pyrrole-2-carboxylic acid.

Step D: Preparation of Methyl 4,10-dihydro-1,7-dimethyl-10-oxo-1H-[1]-benzoxepino[4,3-b]-pyrrole-2-acetate To an ice-bath cooled suspension of 4,10-dihydro-1,7-dimethyl-10-oxo-1H[1]-benzoxepino[4,3-b]-pyrrole-2-carboxylic acid (1.35 g, 0.005 m) in dry methylene chloride (100 ml) containing 1 drop (from capillary tube) anhydrous N,N-dimethylformamide was added thionyl chloride (6.0 ml), and the resulting mixture allowed to warm slowly to room temperature. After stirring at ambient temperatures overnight, the mixture was concentrated in vacuo to a residue, the residue flushed two times with dried benzene (50 ml and 25 ml portions), the residual dried acid chloride taken up in a minimum of dried methylene chloride for solution and added dropwise to an ice-cooled, stirred solution of excess diazomethane in dried ether (prepared from 4 g N-methyl-N-nitrosourea, a 30 ml portion of ether collecting the generated diazomethane) over ca. 2 minutes. After stirring cold for 60 minutes, the mixture was allowed to warm to room temperature and stirred overnight to allow excess diazomethane to escape. Concentration of the reaction mixture yielded the corresponding diazoketone, which was dried and added to a portion of dry methanol (110 ml) which had been stirred for 10 minutes with 0.15 g silver (I) oxide. An additional 0.15 g silver oxide was added and the mixture set immediately in an oil-bath set at 95° C. After 5 minutes, 0.3 g silver oxide plus 0.12 g silver nitrate crystals were added all at once, the mixture refluxed for 1.0 hour, and allowed to cool. After filtering and concentration of the filtrate, the residue was purified via LC (SiO$_2$/15% ethyl acetate-hexane) to yield methyl 4,10-dihydro-1,7-dimethyl-10-oxo-1H-[1]-benzoxepino[4,3-b]-pyrrole-2-acetate.

Step E: Preparation of 4,10-Dihydro-1,7-dimethyl-10-oxo-1H[1]-benzoxepino[4,3-b]pyrrole-2-acetic acid To an ice-cooled suspension of 1.74 g (0.006 m) of methyl 4,10-dihydro-1,7-dimethyl-10-oxo-1H[1]-benzoxepino[4,3-b]pyrrole-2-acetate in a mixture of methanol (50 ml) and water (5 ml) under a nitrogen atmosphere was added 2.5 N sodium hydroxide solution (2.6 cc, 0.0066 m) over 1 minute. After 30 minutes the ice-bath was removed, and the mixture stirred at ambient temperatures for five hours. The mixture was diluted to ca. 150 ml with water, aged, filtered, and the filtrate acidified dropwise with 2.0 N hydrochloric acid. After filtration, washing and drying, 1.5 g of product was obtained which upon recrystallization from i-propanol-water yielded pure 4,10-dihydro-1,7-dimethyl-10-oxo-1H[1]-benzoxepino[4,3-b]-pyrrole-2-acetic acid, m.p. 196°–197° C.

Following essentially the same procedure as described in Steps A to E, but substituting for the sodium m-cresolate (sodium m-phenoxide) used therein, the different phenoxide alkali salts listed below in Table IV, there are prepared various new and appropriately substituted benzoxepino[4,3-b]pyrrole-2-acetic acids also included in Table IV.

TABLE IV

| R | M | R |
|---|---|---|
| 3-CH$_3$O | Na | 7-CH$_3$O |
| 3-CH$_3$S | Na | 7-CH$_3$S |
| 4-C$_2$H$_5$ | Li | 8-C$_2$H$_5$ |
| 3-F | K | 7-F |
| 3-Cl | Na | 7-Cl |

EXAMPLE 5

7-Chloro-4,10-dihydro-1-methyl-10-oxo-1H[1]-benzoxepino[4,3-b]pyrrole-2-acetic acid

Step A: Preparation of Methyl 5-(4-chloro-2-methoxybenzoyl)-1,4-dimethylpyrrole-2-carboxylate Following substantially the same procedure as described in Example 1, Step A, methyl 5-(4-chloro-2-methoxybenzoyl)-1,4-dimethylpyrrole-2-carboxylate was prepared from methyl 1,4-dimethylpyrrole-2-carboxylate (1.53 g, 0.01 m), 4-chloro-2-anisoyl chloride (2.0 g, 0.01 m) and aluminum chloride (2.6 g, 0.02 m) in dichloroethane-nitromethane.

Step B: Preparation of Methyl 7-Chloro-4,10-dihydro-1-methyl-10-oxo-1H[1]-benzoxepino[4,3-b]-pyrrole-2-carboxylate Methyl 5-(4-chloro-2-methoxybenzoyl)-1,4-dimethylpyrrole-2-carboxylate (0.5 g, 0.0015 m) was brominated with N-bromosuccinimide (0.32 g, 0.0018 m) in carbon tetrachloride according to the procedure of Example 4, Step A, to afford methyl 4-(bromomethyl)-5-(4-chloro-2-methoxybenzoyl)-1-methyl-pyrrole-2-carboxylate.

Step C: Preparation of 7-Chloro-4,10-dihydro-1-methyl-10-oxo-1H[1]benzoxepino[4,3-b]-pyrrole-2-acetic acid To a stirred solution of methyl 4-(bromomethyl)-5-(4-chloro-2-methoxybenzoyl)-1-methylpyrrole-2-carboxylate (0.45 g, 0.0011 m) in dry methylene chloride (20 ml) at dry-ice/acetone bath temperature was added boron tribromide (1.3 ml of a 1.0 M solution in methylene chloride) all at once. After 2 hours at these temperatures, the reaction mixture was allowed to warm to 0° C. and kept in a wet-ice bath for an additional 4 hours. Methylene chloride (30 ml) was added, followed by 50 g of ice-water. The mixture was separated, the methylene chloride layer dried and concentrated to crude methyl 4-(bromomethyl)-5-(4-chlorosalicyloyl)-1-methylpyrrole-2-carboxylate which was subsequently dissolved in dry N,N-dimethylformamide (25 ml), stirred and cooled to about −50° C. before sodium hydride (57% suspension in mineral oil, 0.07 g) was added all at once. After 10 minutes, the dry-ice bath was replaced by a wet-ice bath for 2 hours, and the reaction mixture then allowed to rise to room temperature. After 1 hour, excess ether was added, followed by ice-water. The ether layer was separated, dried over sodium sulfate, and concentrated to a white solid. Trituration with hexane yielded methyl 7-chloro-4,10-dihydro-1-methyl-10-oxo-1H[1]benzoxepino[4,3-b]pyrrole-2-carboxylate as a white solid, m.p. 169°–170° C.

Following essentially the same procedures as described in Example 4, Step E, the methylester obtained above was hydrolyzed to 7-chloro-4,10-dihydro-1-methyl-10-oxo-1H-[1]benzoxepino[4,3-b]pyrrole-2-carboxylic acid. Treatment of this carboxylic acid utilizing the same procedures described in Example 4, Steps D and E, yielded 7-chloro-4,10-dihydro-1-methyl-10-oxo-1H[1]benzoxepino[4,3-b]pyrrole-2-acetic acid, m.p. 213° C. dec.

What is claimed is:

1. A process for preparing a compound of formula (II)

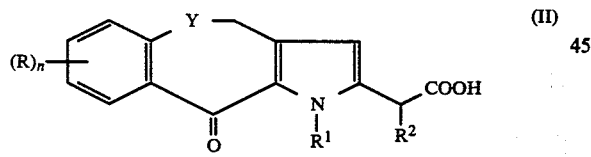

wherein:
Y is O or S;
n is an integer from 1 to 4;
R is
 (a) hydrogen;
 (b) lower alkyl;
 (c) halo-loweralkyl;
 (d) hydroxy or loweralkoxy;
 (e) —OCH$_2$O— when n is 2 and the two Rs join together to form the methylenedioxy group;
 (f) halo;
 (g) lower alkylthio;
 (h) lower alkylsulfinyl;
 (i) lower alkylsulfonyl; or
 (j) lower alkenyl;
$R^1$ is
 (a) hydrogen;
 (b) lower alkyl;
 (c) lower alkenyl;
 (d) aralkyl; and
$R^2$ is
 (a) hydrogen;
 (b) lower alkyl;
 (c) halo; or
 (d) loweralkoxy;
comprising:
 (1) Halogenating a compound of formula (III)

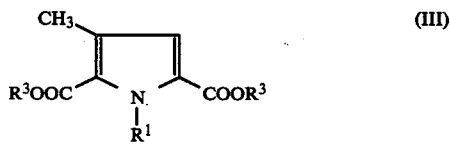

wherein:
$R^1$ is as previously defined; and
$R^3$ is lower alkyl;
 (2) Treating the resultant 4-halomethyl derivative from Step (1) with a compound of formula

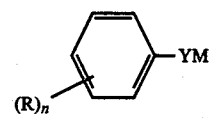

wherein R, n, and Y are as previously defined; and M is an alkali metal cation;
 (3) Hydrolyzing the resultant 4—(R)$_n$C$_6$H$_{5-n}$—Y—CH$_2$-derivative from Step (2) to a diacid of formula (V)

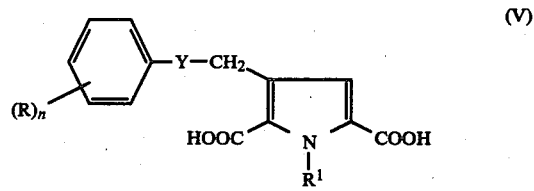

(4) Inducing intramolecular ring closure of the diacid (V) by treatment with a condensing agent to form a tricyclic carboxylic acid of formula (VI)

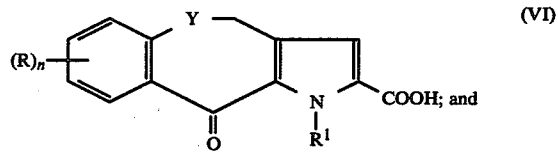

(5) Extending the carboxylic acid side chain of the tricyclic compound (VI) by the Arndt Eistert procedure which further comprises:
  (a) converting the tricyclic carboxylic acid (VI) to its corresponding acid chloride;
  (b) treating the acid chloride with a diazoalkane to form the corresponding diazoketone of compound (VI);
  (c) causing the diazoketone to rearrange to a homologous acid of formula (II) in the presence of a metal salt and a solvent.

2. The process of claim 1 wherein:

Y is O;
n is 1, 2 or 3;
R is
- (a) hydrogen;
- (b) $C_{1-4}$ alkyl;
- (c) halo-$C_{1-3}$alkyl;
- (d) $C_{1-3}$ alkoxy;
- (e) —OCH$_2$O—;
- (f) chloro or fluoro; or
- (g) $C_{1-3}$ alkylthio.

$R^1$ is hydrogen or loweralkyl; and
$R^2$ is hydrogen or loweralkyl.

3. The process of claim 2 wherein
Y is O;
n is 1 or 2;
R is $C_{1-4}$ alkyl or $C_{1-4}$alkoxy;
$R^1$ is $C_{1-3}$ alkyl; and
$R^2$ is hydrogen or methyl.

4. A process for preparing a compound of formula (II)

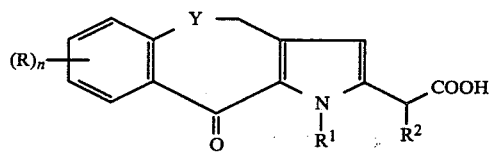

wherein:
Y is O or S;
n is an integer from 1 to 2;
R is
- (a) hydrogen;
- (b) lower alkyl;
- (c) halo-loweralkyl;
- (d) hydroxy or loweralkoxy;
- (e) —OCH$_2$O— when n is 2 and the two Rs join together to form the methylenedioxy group;
- (f) halo;
- (g) lower alkylthio;
- (h) lower alkylsulfinyl;
- (i) lower alkylsulfonyl; or
- (j) lower alkenyl;

$R^1$ is lower alkyl;
$R^2$ is
- (a) hydrogen;
- (b) lower alkyl;
- (c) halo; or
- (d) loweralkoxy;

comprising:
(1) Treating a 1,4-dialkylpyrrole-2-carboxylic acid ester with a compound of formula

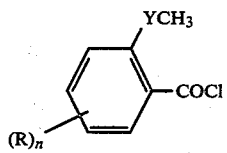

in the presence of a Lewis acid;
(2) Converting the product from Step (1) to a compound of formula IX

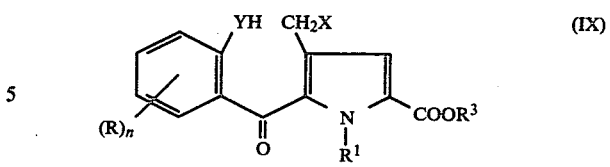

wherein X is halo; by halogenation and subsequent ether cleavage catalyzed by a Lewis acid;
(3) Inducing intramolecular ring closure by treating compound IX with a strong base to form the tricyclic compound of formula (X); and

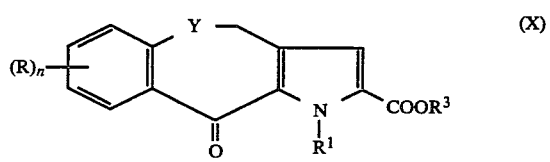

(4) Converting the tricyclic compound (X) to its corresponding acid by hydrolysis; and
(5) Extending the carboxylic acid side chain of the tricyclic compound of step (4) by the Arndt Eistert procedure which further comprises:
- (a) converting the tricyclic carboxylic acid of step (4) to its corresponding acid chloride;
- (b) treating the acid chloride with a diazoalkane to form the corresponding diazoketone of the compound of step (4);
- (c) causing the diazoketone to rearrange to a homologous acid of formula (II) in the presence of a metal salt and a solvent.

5. The process of claim 4 wherein:
Y is O;
n is 1 or 2;
R is
- (a) hydrogen;
- (b) $C_{1-4}$ alkyl;
- (c) halo-$C_{1-3}$alkyl;
- (d) $C_{1-3}$ alkoxy;
- (e) —OCH$_2$O—; or
- (f) chloro or fluoro
- (g) $C_{1-3}$ alkylthio $R^1$ is loweralkyl; and
$R^2$ is hydrogen or loweralkyl.

6. The process of claim 4 wherein:
Y is O;
n is 1;
R is $C_{1-4}$ alkyl or $C_{1-4}$alkoxy;
$R^1$ is $C_{1-3}$ alkyl; and
$R^2$ is hydrogen or methyl.

7. The process of claim 1 wherein M is Na$^+$ or K$^+$ in Step (1).

8. The process of claim 1 wherein the condensing agent in Step (4) is trifluoroacetic anhydride with or without trifluoroacetic acid or a Lewis acid.

9. The process of claim 4 wherein the Lewis acid in Step (1) is AlCl$_3$ or SnCl$_4$.

10. The process of claim 4 wherein the X in Step (2) is bromo; and the strong base in Step (3) is sodium hydride.